(12) United States Patent
Chu et al.

(10) Patent No.: US 12,427,254 B2
(45) Date of Patent: Sep. 30, 2025

(54) DRIVE ASSEMBLY FOR A MEDICAMENT DELIVERY DEVICE

(71) Applicant: SHL MEDICAL AG, Zug (CH)

(72) Inventors: Chun Chu, Taipei (TW); Anders Holmqvist, Värmdö (SE); Erika André, Saltsjö-Boo (SE); Pär Leander, Nacka (SE); Linda Odelberg, Ekerö (SE)

(73) Assignee: SHL Medical AG, Zug (CH)

( * ) Notice: Subject to any disclaimer, the term of this patent is extended or adjusted under 35 U.S.C. 154(b) by 0 days.

(21) Appl. No.: 17/725,206

(22) Filed: Apr. 20, 2022

(65) Prior Publication Data

US 2022/0241506 A1 Aug. 4, 2022

Related U.S. Application Data

(63) Continuation of application No. 16/098,542, filed as application No. PCT/EP2017/060471 on May 3, 2017, now Pat. No. 11,623,045.

(30) Foreign Application Priority Data

May 6, 2016 (SE) .................................. 1650616-4

(51) Int. Cl.
*A61M 5/20* (2006.01)
*A61M 5/315* (2006.01)
(52) U.S. Cl.
CPC ........ *A61M 5/2033* (2013.01); *A61M 5/3155* (2013.01); *A61M 2005/2026* (2013.01); *A61M 2205/581* (2013.01); *A61M 2205/582* (2013.01)

(58) Field of Classification Search
CPC .... A61M 5/3155; A61M 5/2033; A61M 5/31; A61M 5/315; A61M 5/31511;
(Continued)

(56) References Cited

U.S. PATENT DOCUMENTS 7,758,550 B2 7/2010 Bollenbach et al.
11,623,045 B2 * 4/2023 Chu .................... A61M 5/3155
604/136
(Continued)

FOREIGN PATENT DOCUMENTS

CN 101678168 A 3/2010
CN 102481415 A 5/2012
(Continued)

OTHER PUBLICATIONS

International Search Report and Written Opinion for Int. App. No. PCT/EP2017/060471, dated Jul. 11, 2017.

*Primary Examiner* — William R Carpenter
*Assistant Examiner* — Robert F Allen
(74) *Attorney, Agent, or Firm* — McDonnell Boehnen Hulbert & Berghoff LLP

(57) ABSTRACT

A power pack for use with a medicament delivery device is presented having a plunger rod movable along a longitudinal axis; a drive spring operably connected to said plunger rod; a plunger rod sleeve arranged with holding elements for releasably holding said plunger rod with said drive spring in a tensioned state. Signal initiating elements are arranged to said plunger rod; and signal generating elements arranged to cooperate with said signal initiating elements for providing information to a user of a medicament delivery device about the movement of said plunger rod when said plunger rod sleeve has been activated to release said holding elements.

17 Claims, 13 Drawing Sheets

(58) Field of Classification Search
CPC ............ A61M 5/3152; A61M 5/31508; A61M 5/31593; A61M 5/31568; A61M 5/3157; A61M 5/31591; A61M 5/31565; A61M 5/31566; A61M 5/20; A61M 5/31571; A61M 5/3158; A61M 2005/2026; A61M 2005/2086; A61M 2205/581; A61M 2205/582; A61M 5/31573; A61M 5/31526; A61M 2205/43
USPC ........................................................ 604/110
See application file for complete search history.

(56) References Cited

U.S. PATENT DOCUMENTS

| | | | |
|---|---|---|---|
| 2005/0203466 A1 | 9/2005 | Hommann | |
| 2008/0262438 A1* | 10/2008 | Bollenbach | A61M 5/2033 604/207 |
| 2009/0048561 A1* | 2/2009 | Burren | A61M 5/31553 604/135 |
| 2009/0287161 A1 | 11/2009 | Traub et al. | |
| 2010/0137801 A1* | 6/2010 | Streit | A61M 5/2033 604/138 |
| 2011/0245780 A1 | 10/2011 | Helmer et al. | |
| 2012/0029443 A1* | 2/2012 | Holmqvist | A61M 5/20 604/211 |
| 2014/0058320 A1* | 2/2014 | Hansen | A61M 5/31596 604/89 |
| 2014/0180244 A1* | 6/2014 | Arnett | A61M 5/5086 604/506 |
| 2014/0249482 A1* | 9/2014 | Wieselblad | A61M 5/31536 604/211 |
| 2016/0144121 A1 | 5/2016 | Oakley et al. | |
| 2016/0287802 A1* | 10/2016 | Blancke | A61M 5/31575 |
| 2016/0296706 A1* | 10/2016 | Blancke | A61M 5/24 |
| 2017/0354779 A1* | 12/2017 | Atterbury | A61M 5/3157 |

FOREIGN PATENT DOCUMENTS

| | | |
|---|---|---|
| CN | 102917738 A | 2/2013 |
| CN | 103945879 A | 7/2014 |
| EP | 2438944 A1 | 4/2012 |
| EP | 2438947 A1 | 4/2012 |
| EP | 2583705 A1 | 4/2013 |
| JP | 2008229344 A | 10/2008 |
| JP | 2012-532635 A | 12/2012 |
| JP | 2013-526904 A | 6/2013 |
| JP | 2013-534164 A | 9/2013 |
| WO | 2003053499 A1 | 7/2003 |
| WO | 2005009515 A1 | 2/2005 |
| WO | 2007131013 A1 | 11/2007 |
| WO | 2007131025 A1 | 11/2007 |
| WO | 2009114542 A1 | 9/2009 |
| WO | 2009137486 A1 | 11/2009 |
| WO | 2010017650 A1 | 2/2010 |
| WO | 2010023481 A1 | 3/2010 |
| WO | 2010149214 A1 | 12/2010 |
| WO | 2011/003979 A1 | 1/2011 |
| WO | 2011003980 A1 | 1/2011 |
| WO | 2011039231 A1 | 4/2011 |
| WO | 2011048223 A1 | 4/2011 |
| WO | 2011/123024 A1 | 10/2011 |
| WO | 2012/022810 A2 | 2/2012 |
| WO | 2012163890 A1 | 12/2012 |
| WO | 2013016832 A1 | 2/2013 |
| WO | 2013/034985 A2 | 3/2013 |
| WO | 2013092670 A1 | 6/2013 |
| WO | 2013156516 A1 | 10/2013 |
| WO | 2013169800 A1 | 11/2013 |
| WO | 2014/166919 A1 | 10/2014 |
| WO | 2015087090 A2 | 6/2015 |
| WO | 2015/121081 A1 | 8/2015 |
| WO | 2015166286 A2 | 11/2015 |
| WO | 2016/034407 A2 | 3/2016 |

* cited by examiner

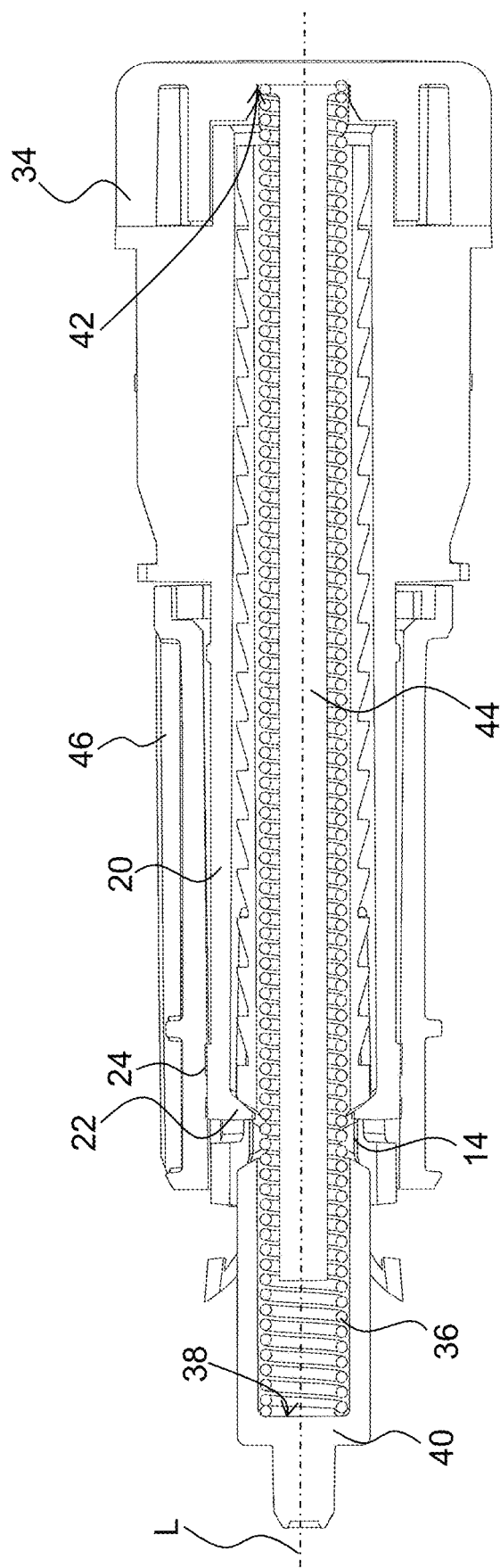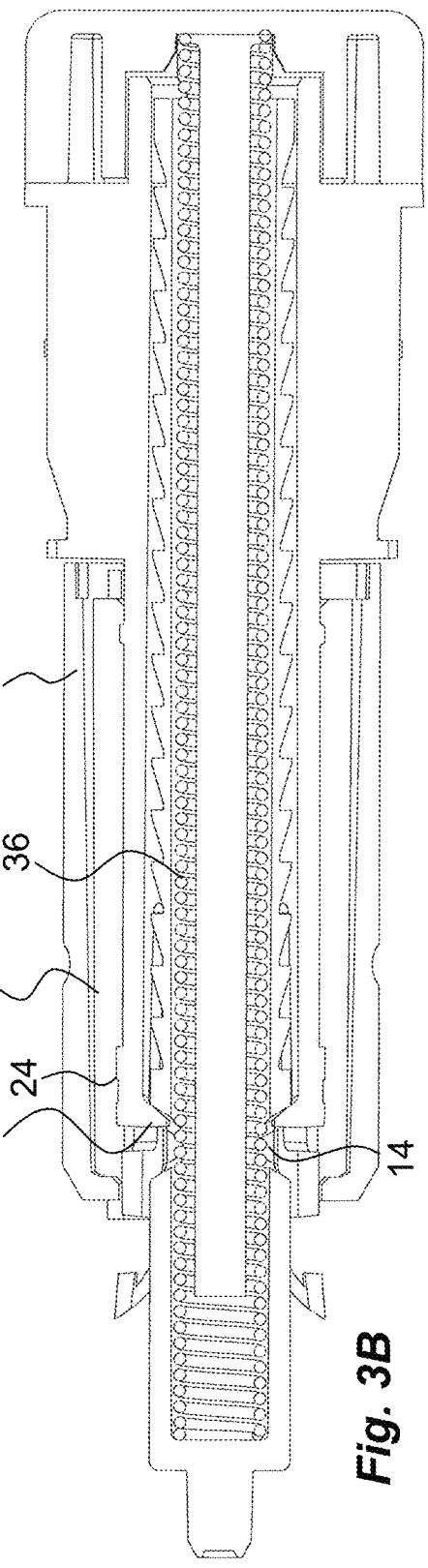
Fig. 3A
Fig. 3B

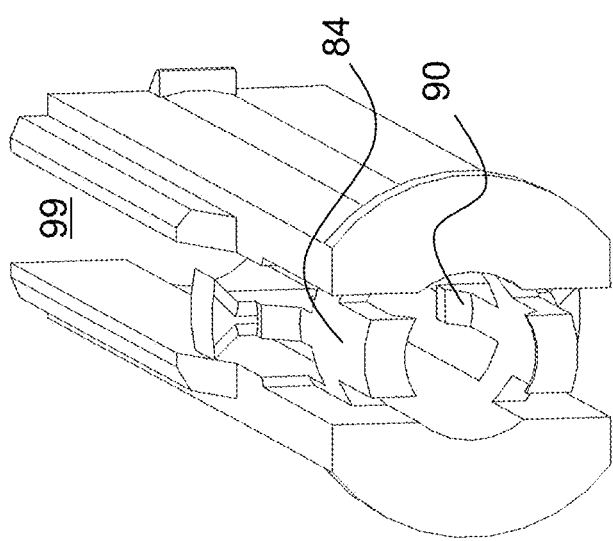
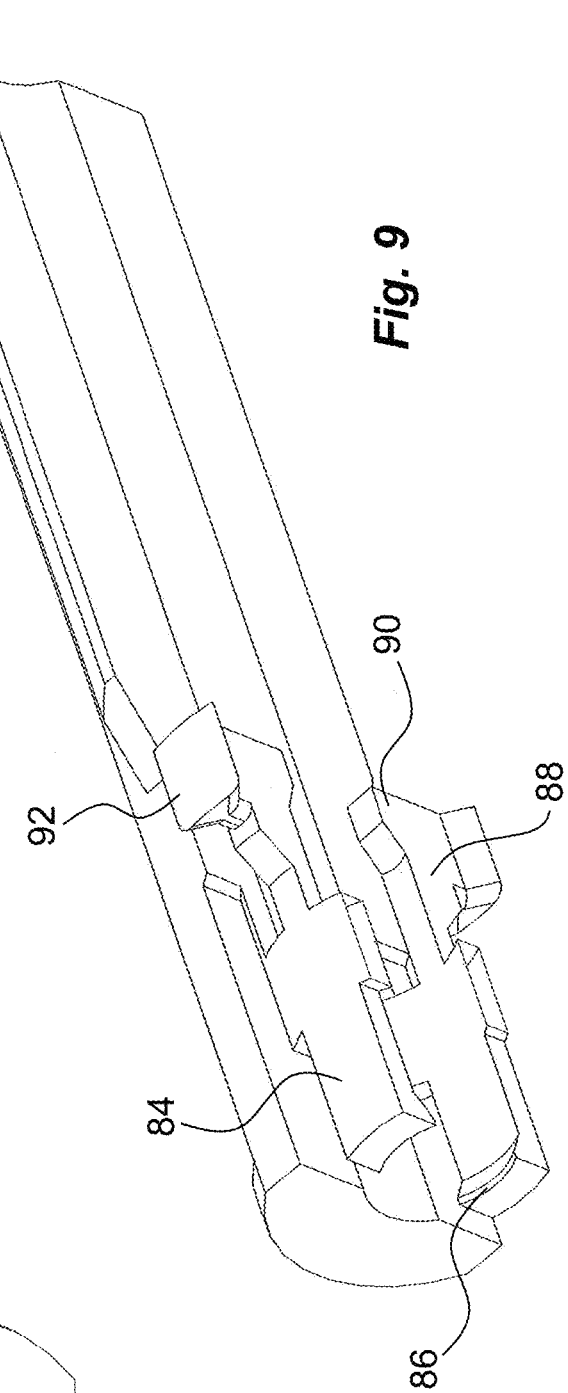

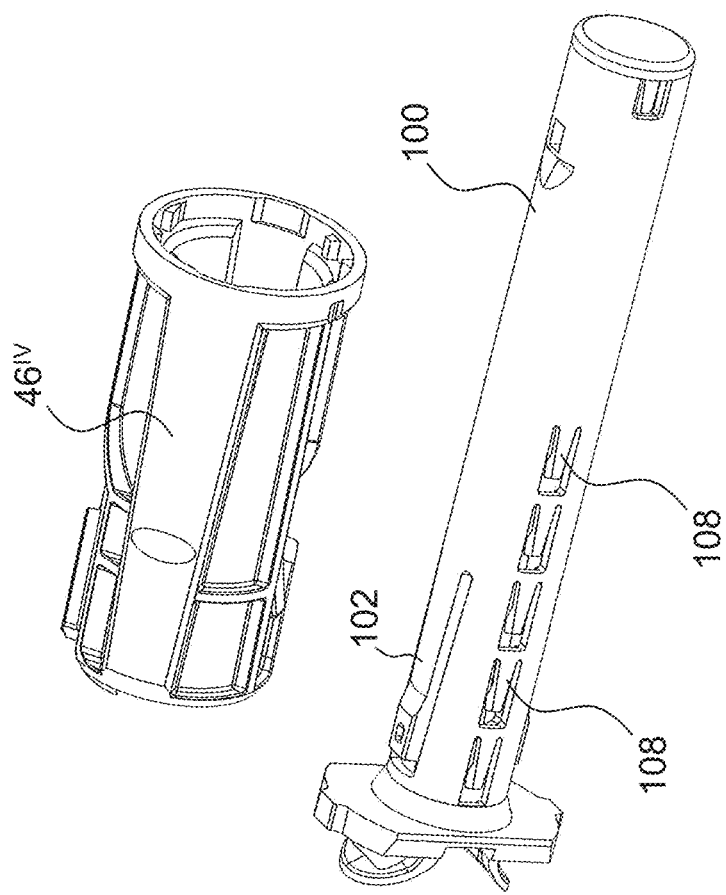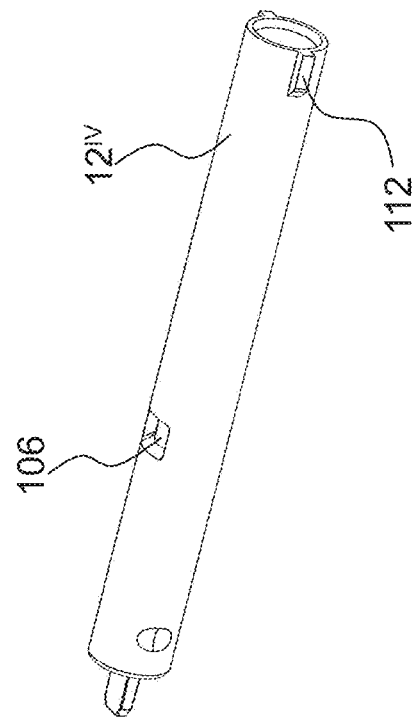
Fig. 11

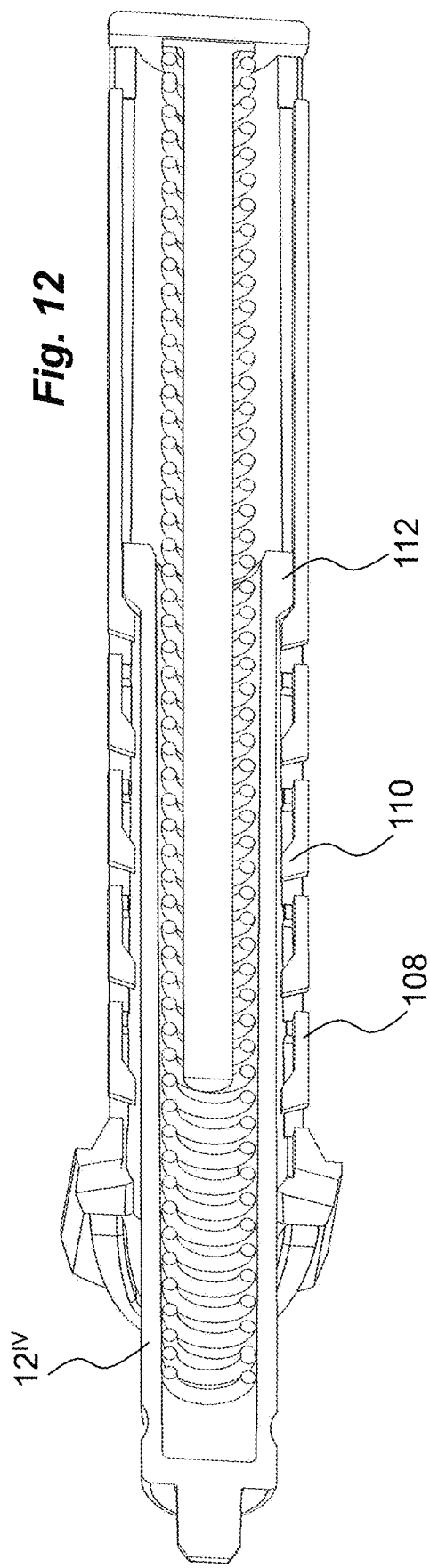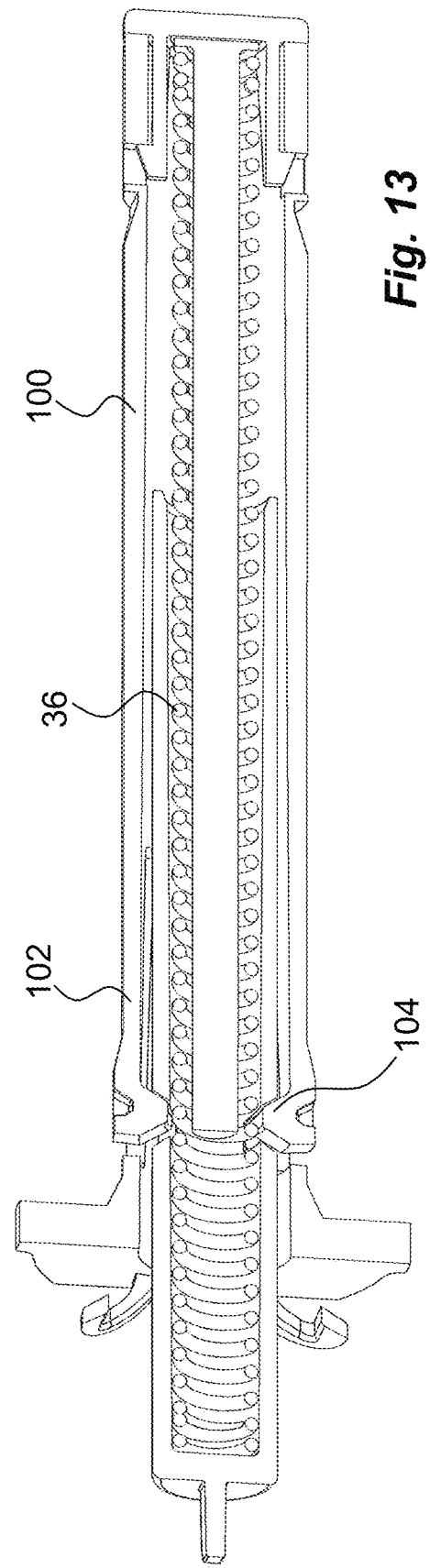

DRIVE ASSEMBLY FOR A MEDICAMENT DELIVERY DEVICE

CROSS REFERENCE TO RELATED APPLICATIONS

The present application is a continuation of U.S. patent application Ser. No. 16/098,542, filed Nov. 2, 2018, which is a U.S. National Phase Application pursuant to 35 U.S.C. § 371 of International Application No. PCT/EP2017/060471 filed May 3, 2017, which claims priority to Sweden Patent Application No. 1650616-4 filed May 6, 2016. The entire disclosure contents of these applications are herewith incorporated by reference into the present application.

TECHNICAL FIELD

The present disclosure relates to a power pack for a medicament delivery device capable of providing energy for expelling doses of medicament from medicament containers.

BACKGROUND

Many medicament delivery devices on the market have been developed for self-administration of medicament to users. Since many of these users generally are not experienced in handling medicament delivery devices and there often is an amount of anxiety and reluctance in the self-administration, especially regarding injection medicament delivery devices, the developers of medicament delivery devices often try to design them with a large degree of functionality as well as features that conceal or minimize the exposure of injection needles.

Another problem often accompanied with medicament delivery devices for self-administration is the correct handling in order to ascertain that the user receives the full and intended dose of medicament as well as to minimize the risk of failures and even accidents. In that regard it is important that the device is easy to handle but also that the user receives information both before and during use. For instance it is important that the medicament delivery device is not removed prematurely from a dose delivery site, which may be a problem as such because of the discomfort of using the device wherein the user wants to remove the medicament delivery device as soon as possible.

For this purpose a number of signalling or information providing solutions have been developed, where many of these concern information during and/or at the end of a dose delivery sequence in order to provide the user when it is safe to remove the medicament delivery device.

Document U.S. Pat. No. 7,758,550 discloses a medicament delivery device with a signalling unit. The signalling unit comprises a catch rod connected to a switch sleeve, and an engaging sleeve which surrounds the catch rod and is axially and fixedly connected, e.g. latched with a first latching element, to a piston rod.

At the start of the delivery movement, the catch rod and the engaging sleeve, provided with an engaging element, are drawn even further apart, such that the engaging element is moved over a section that is provided with latching elements, such that the latching elements are respectively passed over by the engaging element. A brief clicking signal is emitted as each of the latching elements is passed over by the engaging element.

The drawback with the solution according to U.S. Pat. No. 7,758,550 is that in order to provide the signal, a number of additional components are needed apart from the components that are normally present in medicament delivery devices.

SUMMARY

In the present application, the term "distal part/end" refers to the part/end of the device, or the parts/ends of the members thereof, which under use of the device, is located the furthest away from a delivery site of a user. Correspondingly, the term "proximal part/end" refers to the part/end of the device, or the parts/ends of the members thereof, which under use of the device is located closest to the delivery site of the user.

The aim of the present disclosure is to remedy the drawbacks of the state of the art medicament delivery devices and to provide a medicament delivery device having a signalling function that is reliable, clearly understandable and that minimizes the need and use of additional components.

The aim is solved by a medicament delivery device provided with the features according to the independent patent claim. Preferable embodiments form the subject of the dependent patent claims.

According to the disclosure the power pack that is to be used with a medicament delivery device may comprise a plunger rod movable along a longitudinal axis, a drive spring operably connected to said plunger rod, a plunger rod sleeve arranged with holding elements for releasably holding said plunger rod with said drive spring in a tensioned state.

These features are common in many different medicament delivery devices that use pre-tensioned drive springs for delivering doses of medicament. The activation of the power pack may be performed in many ways, manually automatically or semi-automatically.

According to a preferable solution signal initiating elements are arranged on the plunger rod and there are further provided signal generating elements that are arranged to cooperate with the signal initiating elements for providing information to a user of a medicament delivery device about the movement of said plunger rod when the actuator sleeve has been activated to release said holding elements.

With this solution, the plunger rod is used directly for initiating signals to a user for informing him or her about movement of the plunger rod, which is a clear indication of a dose delivery operation. It is an advantage to use the plunger rod more or less directly, which reduces the number of components while providing additional functionality besides the dose delivery function.

According to one feasible solution, the signalling elements may comprise a number of protrusions arranged after each other along the longitudinal axis. These protrusions may be produced directly on the surface of the plunger rod when manufactured. In this respect, the protrusions may be arranged with equal distance after each other. On the other hand, the protrusions may instead be arranged with decreased distance after each other in the proximal direction, or there could be a mix of the two depending on the intended information to the user. For instance, equal distance between the protrusions will result in a decreasing signal frequency because the power from the spring will decrease as the dose delivery sequence progresses.

On the other hand, a decreased distance between the protrusions may, with the same spring, create a constant signal frequency depending on the balance between the decrease in force and decrease in distance. A further scenario is that the frequency increases at the end of a dose delivery sequence, again depending on the balance between the force of the spring and the decrease in distance.

In order to provide distinct signals, the protrusions may be designed with wedge-shapes. With this type of shape and when the signal generating elements may comprise mechanical flexible elements that mechanically engage with said signal initiating elements for providing information, then a very clear and distinct signalling is obtained.

As an alternative to protrusions, a number of cut-outs may be arranged along the longitudinal axis of the plunger rod. further, in order to keep the number of additional components as low as possible, the signal generating elements may comprise the holding elements of said actuator. With this solution, the holding elements will have a dual function in that they first hold the plunger rod in the loaded state and then after release of the plunger rod, generate the signals that indicate the progress of the dose delivery operation.

In order to provide a good grip for holding the plunger rod, as well as providing clear and distinct signals, the holding elements may comprise generally longitudinally extending, flexible, arms, where the arms may be arranged with ledges designed to engage recesses of the plunger rod, which ledges are arranged to cooperate with the signal initiating elements. Moreover, the signal generating elements may comprise a plurality of mechanical flexible elements placed after each other in the longitudinal direction in at least one row. With this solution the number of signal generating elements is higher than the number of signal initiating elements. For example, it requires only one protrusion for generating signals when passing and contacting the row of signal generating elements.

With the solutions described above, the information may comprise audible information as well as tactile information in that both sound and vibrations may be created by the signal generating elements cooperating with the signal initiating elements.

According to a further feasible solution of the power pack, it may further comprise an actuator arranged coaxially outside the plunger rod sleeve, where the actuator is movable from a blocking position to a release position. The movement of the actuator from the blocking position to the release position may be rotatable and/or movable along the longitudinal axis.

These and other aspects of, and advantages with, the present disclosure will become apparent from the following detailed description of the disclosure and from the accompanying drawings.

BRIEF DESCRIPTION OF DRAWINGS

In the following detailed description of the disclosure, reference will be made to the accompanying drawings, of which FIG. 3A is a cross-sectional view of the power pack of FIG. 1, FIG. 3B is a cross-sectional view of the power pack of FIG. 1, FIG. 8 is a detailed view of a plunger rod sleeve comprised in the third embodiment, FIG. 9 is a detailed view of a plunger rod sleeve comprised in the third embodiment, FIG. 11 is an exploded view of a fourth embodiment of a power pack, FIG. 12 is a cross-sectional view of the power pack of FIG. 11, FIG. 13 is a cross-sectional views of the power pack of FIG. 11.

DETAILED DESCRIPTION

Figure 1:
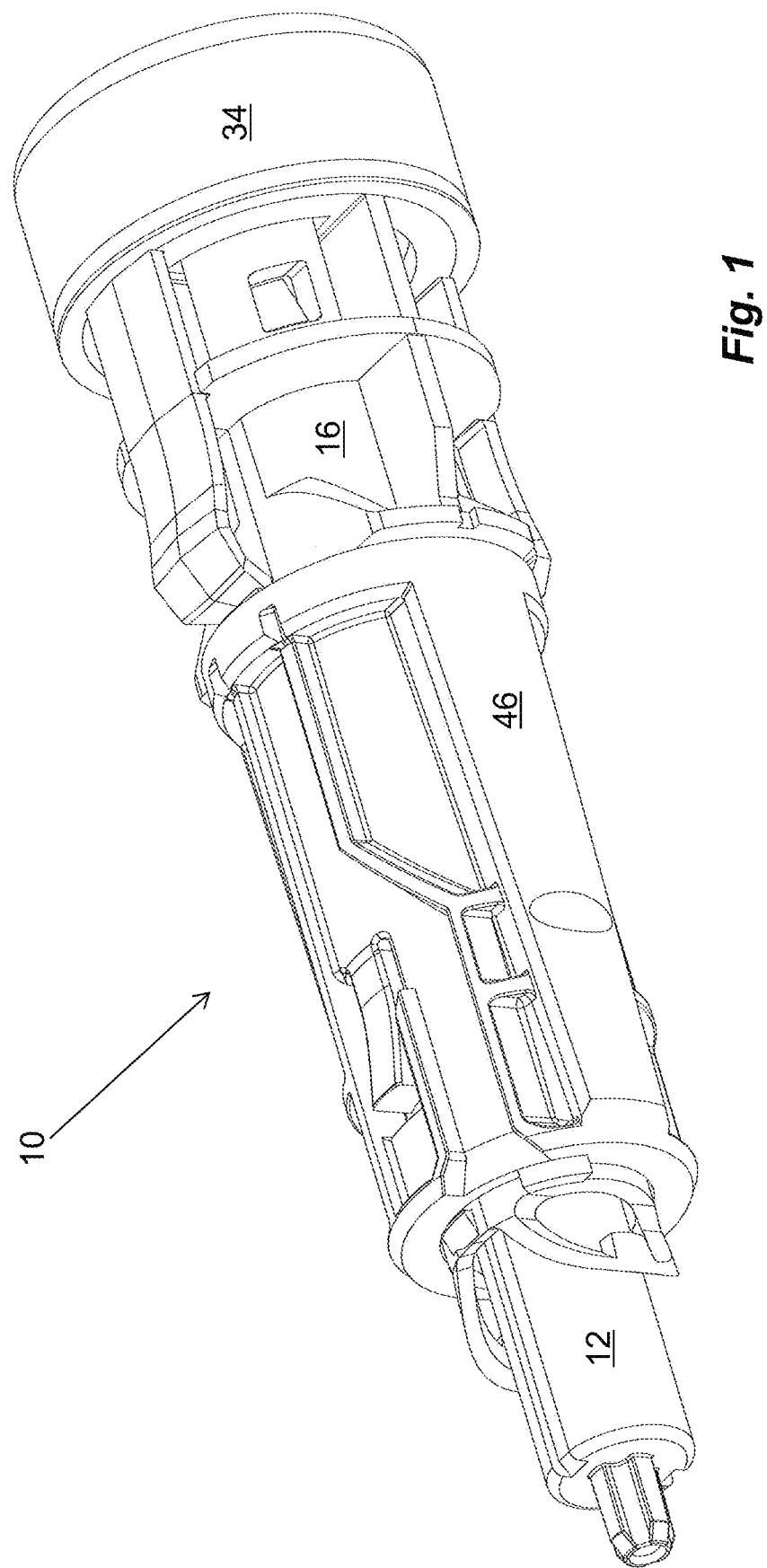
FIG. 1 is a perspective view of a power pack according to the disclosure.
Figure 2:
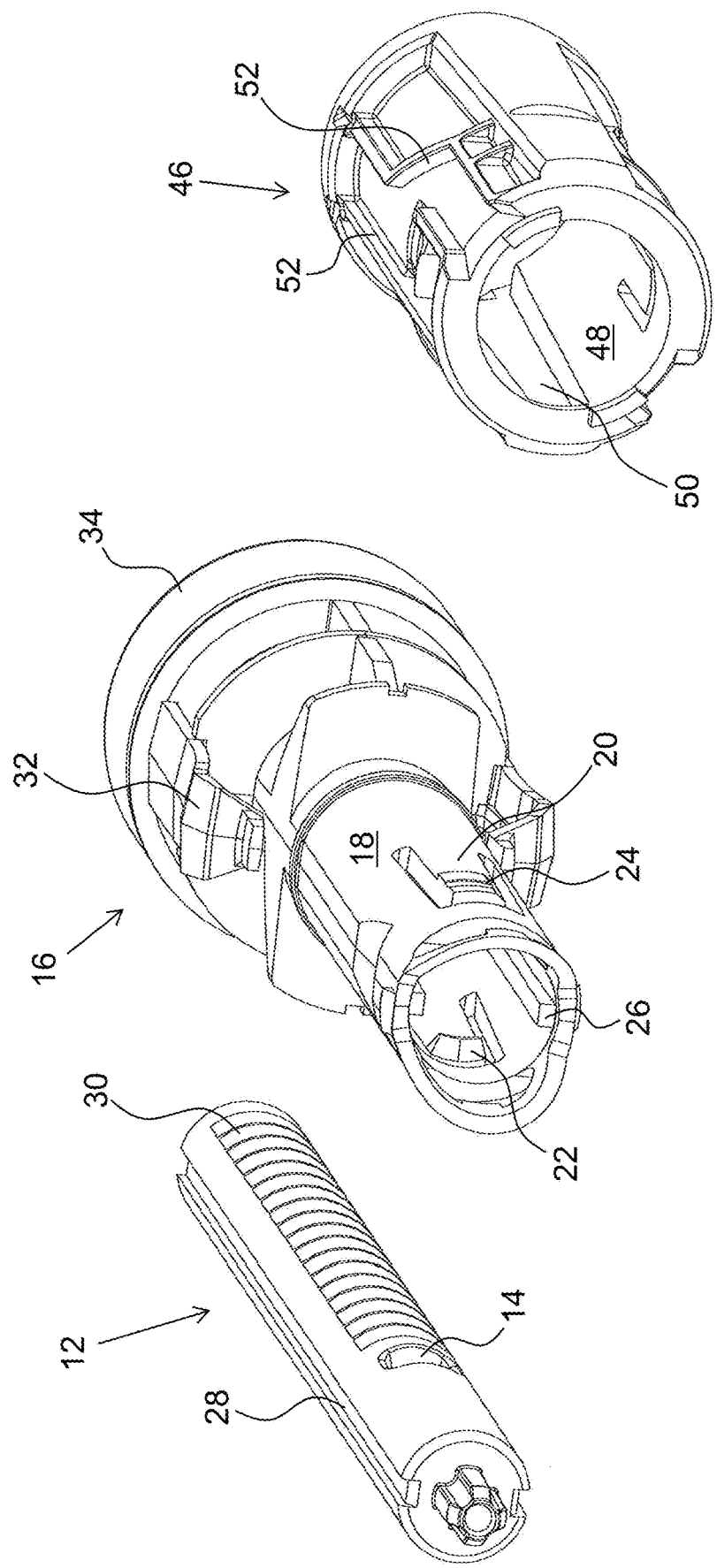
FIG. 2 is an exploded view of the power pack of FIG. 1.

A power pack 10 shown in the drawings is designed to fit into a medicament delivery device designed to deliver a dose of medicament to a patient or user. The power pack 10, FIGS. 1 and 2, comprises an elongated plunger rod 12 arranged to act on a stopper of a medicament container (not shown) for expelling a dose of medicament. The plunger rod 12 is arranged with recesses 14 on its side surfaces, two in the embodiment shown and placed on opposite sides of the plunger rod 12. Outside and coaxial with the plunger rod 12 is a plunger rod holder 16 arranged. It comprises a generally tubular proximal part 18, which proximal part 18 is arranged with holding elements in the form of arms 20 that are flexible in the generally radial direction. The free ends of the arms 20 are arranged with radially inwardly extending ledges 22, which ledges 22 are arranged to fit into the recesses 14 of the plunger rod 12, for releasably holding the plunger rod 12. The free ends of the arms 20 are further arranged with radially outwardly directed protrusions 24. The inner surface of the proximal part 18 of the plunger rod holder 16 is arranged with longitudinally extending ledges 26, which ledges 26 are configured to interact with longitudinal grooves 28 on the outer surface of the plunger rod 12, providing a rotational lock between the plunger rod holder 16 and the plunger rod 12, yet allowing longitudinal movement between them. Further, the plunger rod 12 is arranged with signal initiating elements that in the embodiment shown are arranged as rows of wedge-shaped protrusions 30, which wedge-shaped protrusions 30 are intended to interact with the inwardly extending ledges 22 of the arms 20 of the plunger rod holder 16 as will be described.

The distal end of the plunger rod holder 16 is arranged with attachment elements 32 that are designed to attach the plunger rod holder 16 to a suitable housing of the medicament delivery device. The distal end of the plunger rod holder 16 may then be arranged with an end cap 34 that fits with the housing. A drive spring 36, FIG. 3, that in the embodiment shown is a compression spring is provided inside the hollow plunger rod 12 between a distally directed surface 38 of a proximal end wall 40 of the plunger rod 12 and a proximally directed surface 42 of the end cap 34, which is fixed in relation to the plunger rod holder 16. A guide rod 44 is further arranged inside the drive spring 36 for preventing buckling of the drive spring 36 during activation.

Outside and coaxial with the actuator is a generally tubular actuator 46, which actuator sleeve will act as an activator of the power pack as will be described. The actuator 46 is on its inner surface arranged with inwardly directed surfaces 48 that will function as blocking elements for the holding elements as will be described. Further the inner surface of the actuator 46 is arranged with longitudinally extending recesses 50, in the embodiment two recesses 50, that are arranged on opposite sides of the inner surface. The outer surface of the actuator 46 is further arranged with guide ledges 52, where some sections of the guide ledges 52 are extending longitudinally, and some sections are arranged with an inclination in relation to a longitudinal axis L.

The device is intended to function as follows. When the power pack 10 is in its powered, ready to use state, the plunger rod 12 is pushed into the plunger rod holder 16 from the proximal end, tensioning the drive spring 36. The arms 20 of the plunger rod holder 16 then enter the recesses 14 of the plunger rod 12, thereby holding the plunger rod 12 in the tensioned state. In order for the arms 20 not to flex out of engagement with the recesses 14 of the plunger rod 12, the actuator 46 is placed outside the plunger rod holder 16, whereby the outwardly directed protrusions 24 of the arms 20 of the actuator abut the inwardly directed surfaces 48 of the actuator 46, thereby preventing radial outward movement of the arms, FIG. 3a.

The power pack 10 is then assembled with a suitable housing accommodating a medicament container, which in turn is provided with a medicament delivery member. When the power pack 10 is to be activated, preferably after a medicament delivery member has been placed at a dose delivery site, such as an injection needle penetrating the skin of a patient or user, the actuator 46 is operated, functioning as an activator. This is done by turning the actuator 46 in relation to the plunger rod holder 16. The turning may be performed in many ways, such as by an activation button operated manually by a user or by a medicament delivery member guard that is contacting the dose delivery site and is moved distally in relation to the medicament delivery device and the actuator sleeve. Appropriate elements may then cooperate with the inclined guide ledges of the actuator 46 for providing a rotation of the latter.

The turning of the actuator 46 will cause the longitudinal recesses 50 of the actuator sleeve 46 to be moved in line with the arms 20 with their outwardly directed protrusions 24, FIG. 3b. This releases the arms 20 so that they can flex outwards whereby the inwardly directed ledges 22 will move out of engagement with the recesses 14 of the plunger rod 12. The plunger rod 12 is now urged in the proximal direction by the force of the drive spring 36 whereby the plunger rod 12 will act on the stopper of the medicament container such that a dose of medicament is delivered.

Figure 4:
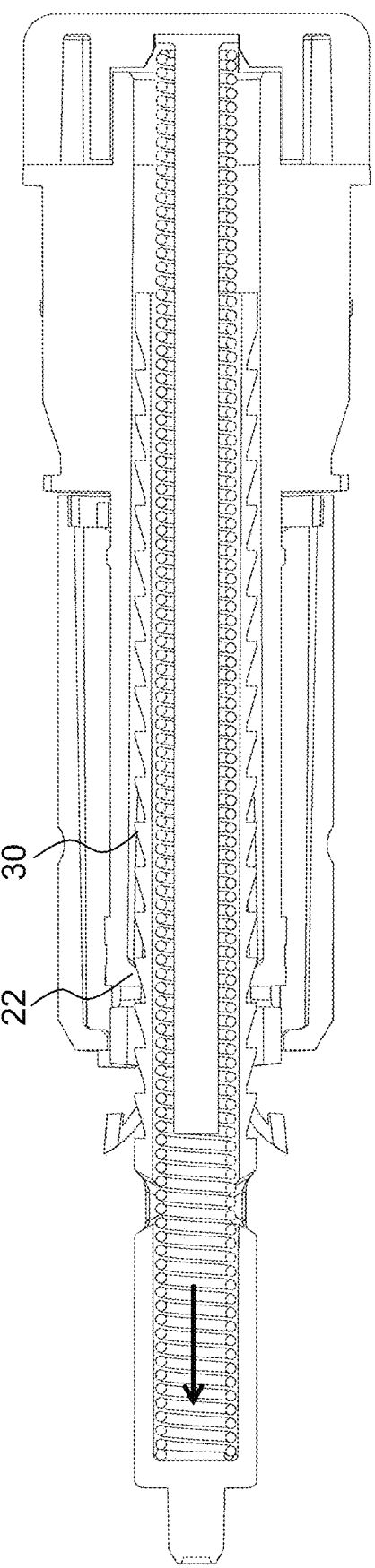
FIG. 4 is a cross-sectional view during activation of the power pack of FIG. 1.

During the movement of the plunger rod 12 in the proximal direction during the dose delivery sequence, the inwardly directed ledges 22 of the arms 20 will be in contact with and slide along the plunger rod 12, FIG. 4. The ledges 22 will then come in contact with the rows of wedge-shaped protrusions 30 and will move along these, causing a rattling sound as well as vibration, i.e. audible and tactile information to the user during the dose delivery sequence. The longitudinal ledges 26 on the plunger rod holder 16 cooperate with the grooves 28 on the plunger rod 12 for preventing the plunger rod 12 from turning during the movement, which otherwise would risk that the ledges 22 of the arms 20 would be moved out of engagement with rows of protrusions 30.

In the embodiment shown, the row of wedge-shaped protrusions 30 extends along a majority of the length of the plunger rod 12. It is however to be understood that the row of protrusions 30 may be arranged such that they engage with the ledges 22 of the arms 20 only at the end of a dose delivery sequence or during the latter half of the dose delivery sequence for just informing the user that the dose delivery sequence is about to terminate. It is of course to be understood that the signalling elements may have other shapes for creating the desired signalling to a user. Also the length between each subsequent protrusion, and thus the frequency of the sound, or vibration, may be modified in order to vary the signalling. In this respect the frequency may be altered during the dose delivery sequence, e.g. increasing the frequency during the progress of the dose delivery sequence.

Figure 5:
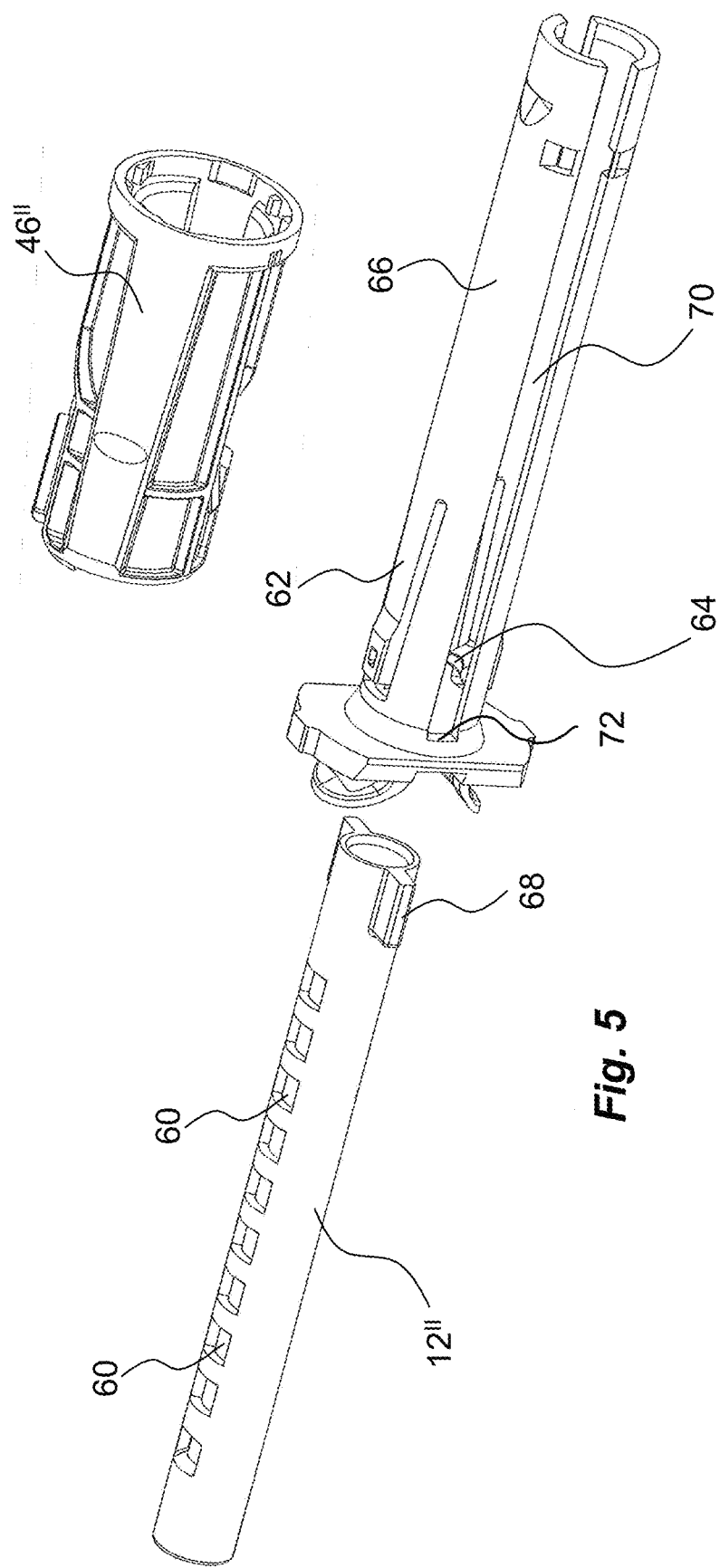
FIG. 5 is an exploded view of a second embodiment of a power pack.
Figure 6:
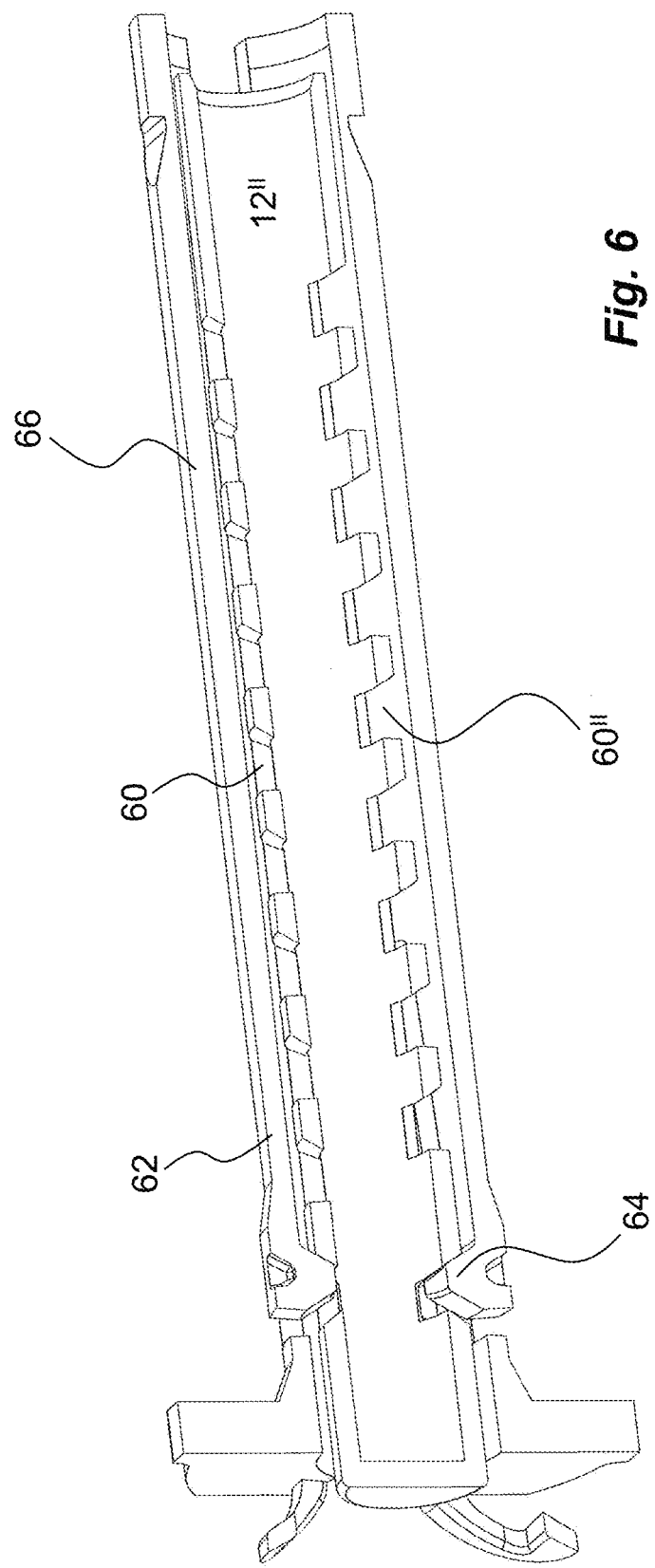
FIG. 6 is a cross-sectional view of the power pack of FIG. 5.
Figure 7:
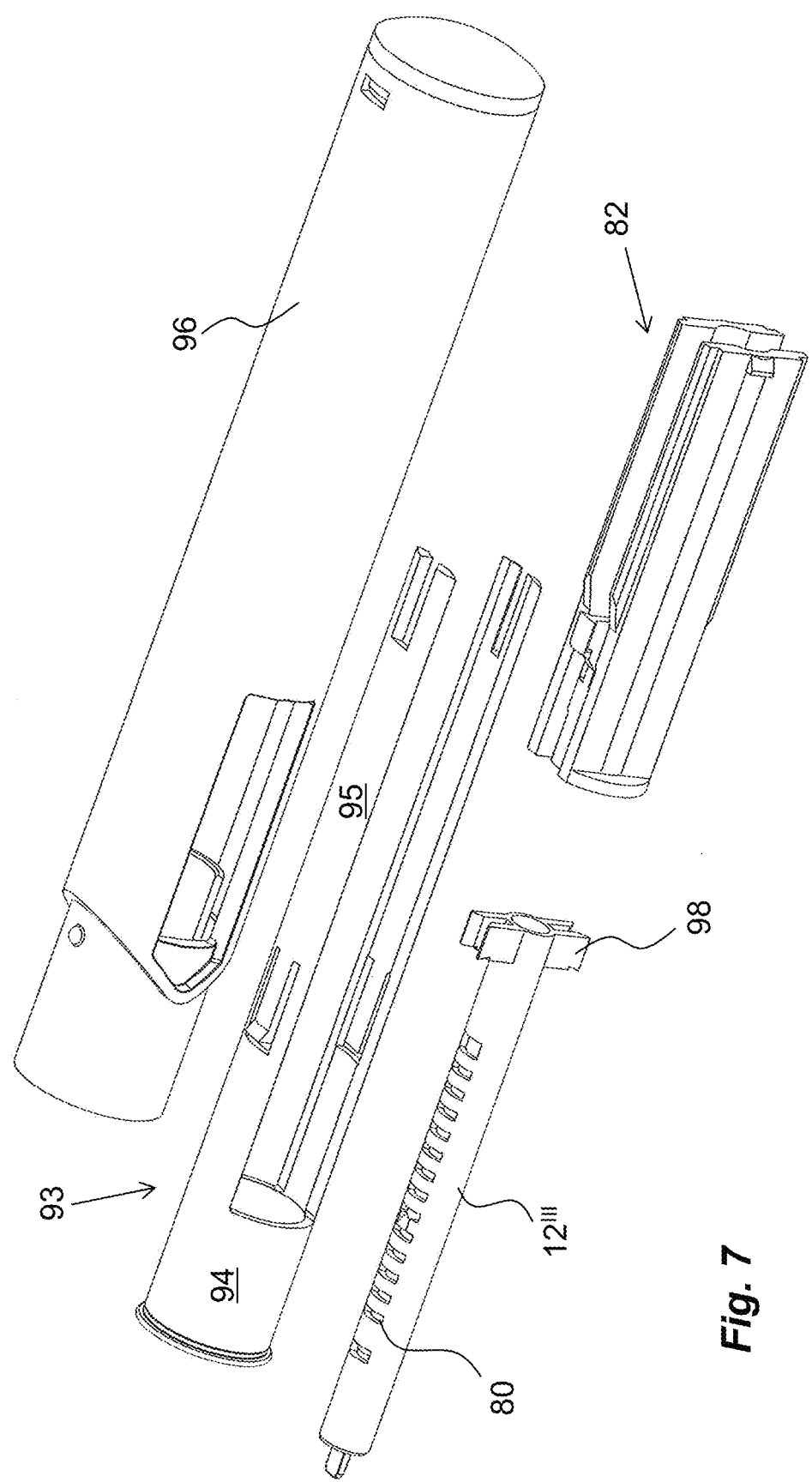
FIG. 7 is an exploded view of a third embodiment of a power pack.

A second alternative is shown in FIGS. 5-6. Here the signal initiating elements comprise at least one row of cut-outs 60 along the plunger rod $12^{II}$. The signal generating elements are here arms 62 that are flexible in the generally radial direction and directed proximally. The free ends of the arms 62 are arranged with inwardly directed protrusions 64 that will engage the cut-outs 60. The signal generating elements are attached to or made integral with a generally tubular and elongated plunger rod sleeve 66. The outer surfaces of the arms 62 will cooperate with an actuator $46^{II}$ for releasingly holding the arms and thereby the tensioned plunger rod $12^{II}$. Moreover, there could be a second row of cut-outs $60^{II}$, for example on the opposite side of the plunger rod $12^{II}$. This could be used for creating a more frequent sound generation wherein one row is displaced half a step in the axial direction. With this solution the sounds appear twice as many times.

Further in order to ensure the relative positions between the row or rows of cut-outs and the protrusions on the arms, the plunger rod $12^{II}$ is arranged with a number of laterally extending protrusions or wings 68, which wings fit into longitudinal guide slots 70 in the plunger rod sleeve 66. The guide slots 70 are further preferably arranged with stop surfaces 72 at a proximal area of the plunger rod sleeve 66. This ensures that a tensioned plunger rod $12^{II}$ cannot shoot out of the plunger rod sleeve 66 during assembly of the power pack.

Further, even though it is an advantage to use the arms of the plunger rod holder not only for holding the plunger rod, but also to create the information to the user, in some instances there could be separate elements that are in contact with the rows of protrusions, causing the sound and the vibrations.

Figure 10:
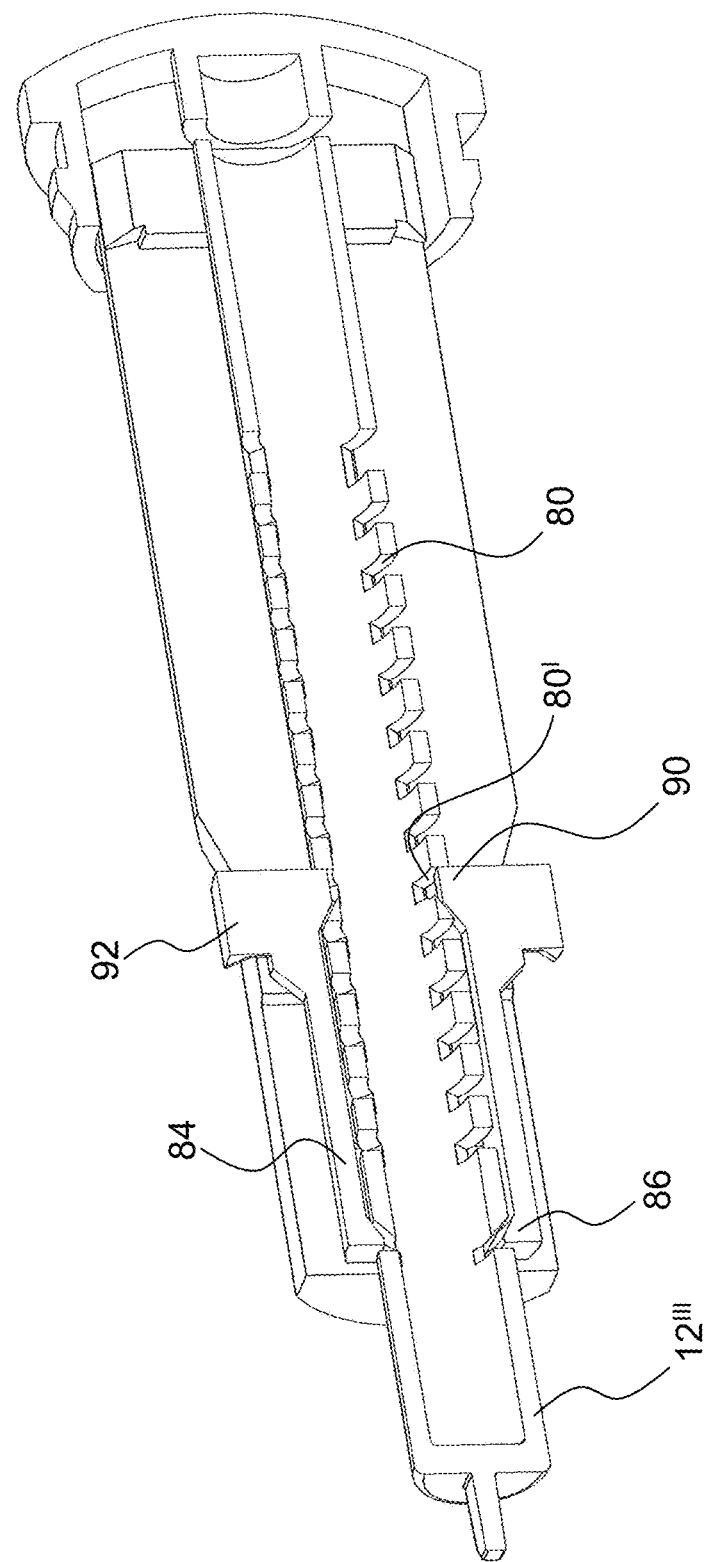
FIG. 10 is a cross-sectional view of the power pack of FIG. 7.
Figure 14:
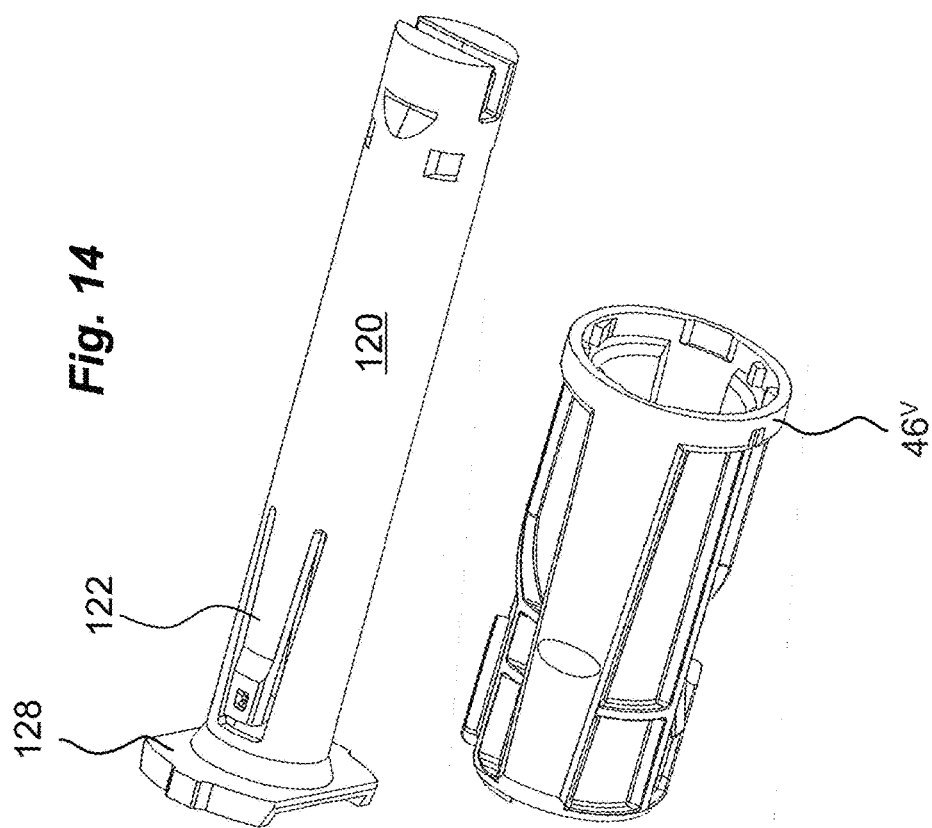
FIG. 14 is an exploded view of a fifth embodiment of a power pack.
Figure 15:
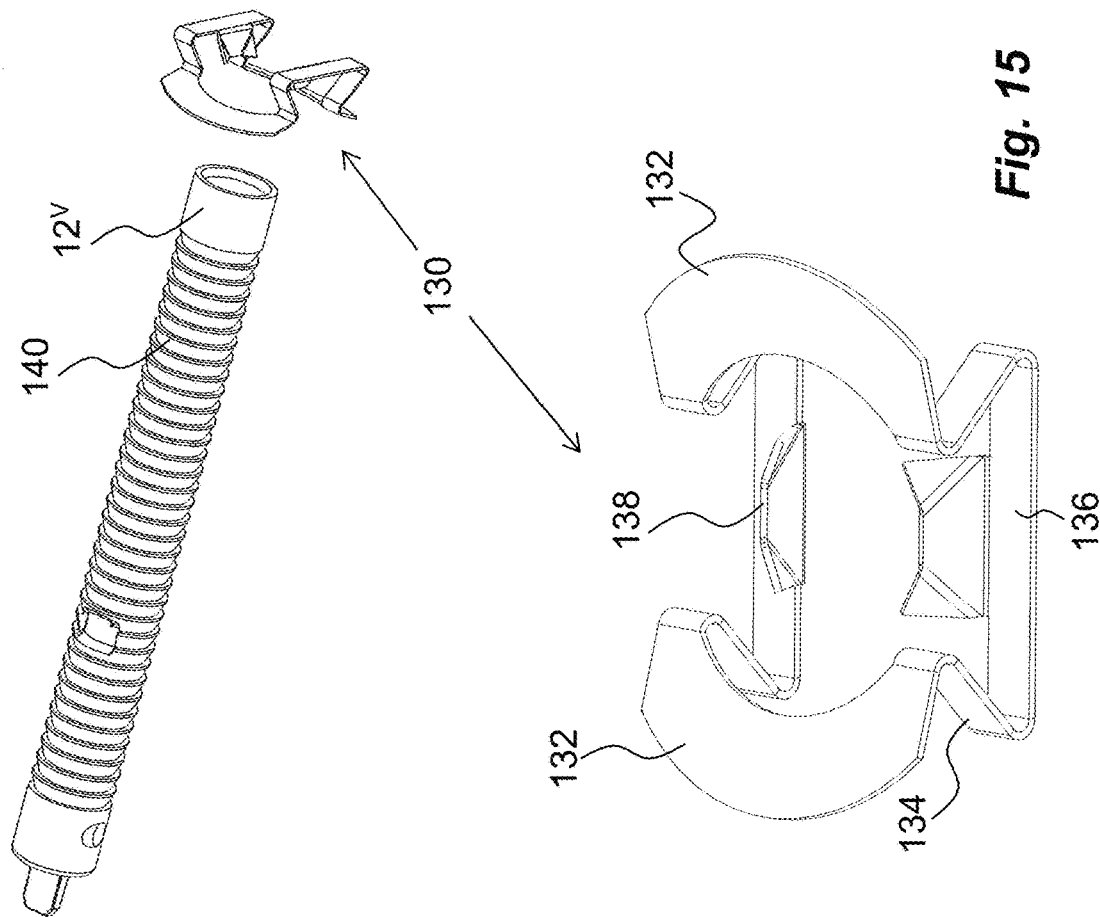
FIG. 15 is a detailed view of a signal generating mechanism of the power pack of FIG. 14.
Figure 16:
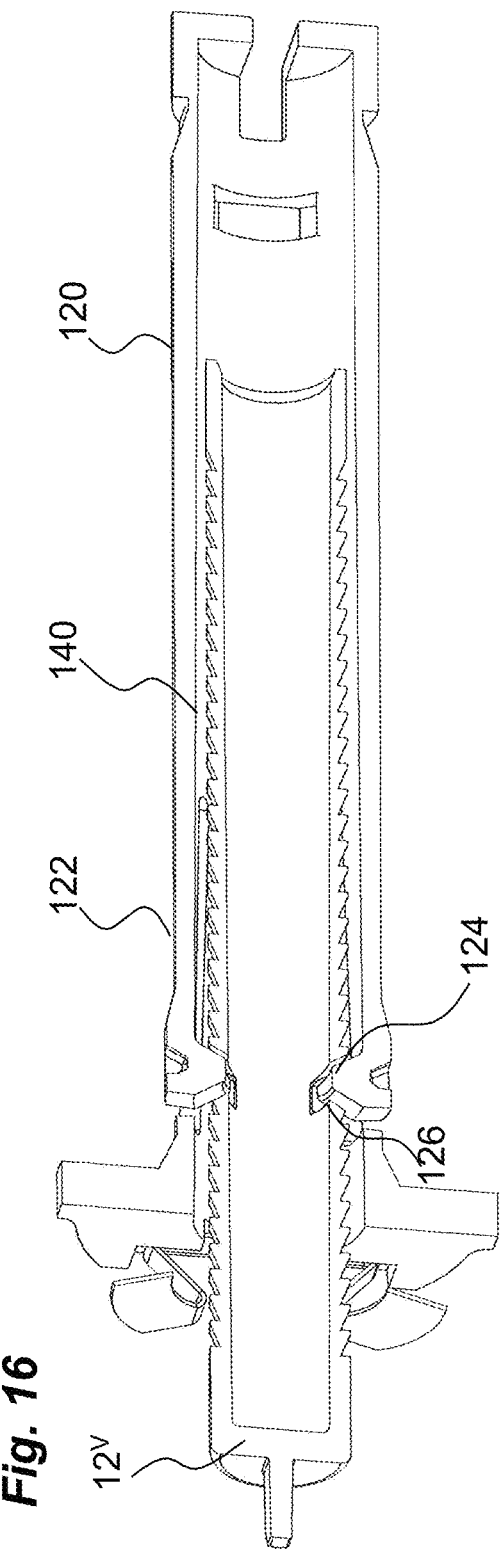
FIG. 16 is a cross-sectional view of the power pack of FIG. 14.
Figure 17:
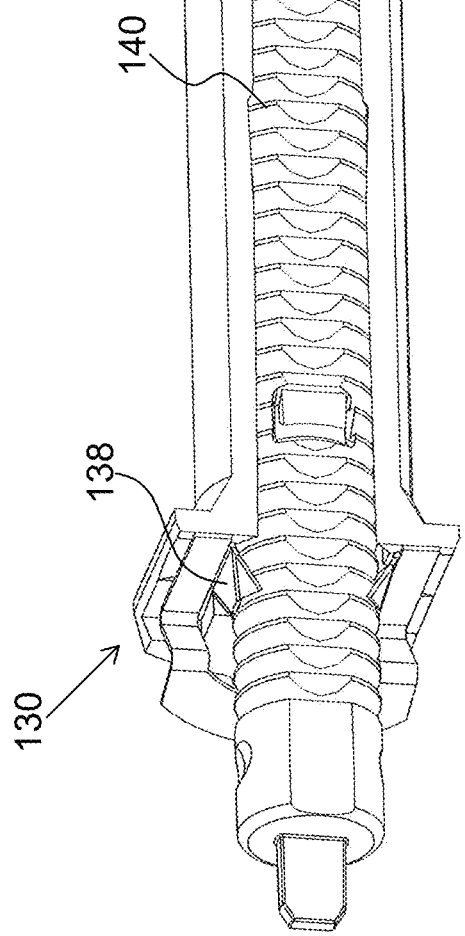
FIG. 17 is a cross-sectional view of the power pack of FIG. 14.

This variant is displayed in FIGS. 7-10 that show a third embodiment of a power pack. As with the second embodiment, a plunger rod $12^{III}$ is provided with a number of signal initiating elements in the form of a number of cut-outs 80 placed in rows in the longitudinal direction of the plunger rod $12^{III}$, in the embodiment shown two rows of cut-outs 80 placed on opposite sides of the plunger rod $12^{III}$. The plunger rod $12^{III}$ is arranged to slide in a plunger rod sleeve 82. Moreover, the plunger rod sleeve 82 is arranged with proximally directed signal generating elements in the form of proximally directed arms 84, FIGS. 8 and 9, which arms 84 are provided with inwardly directed protrusions 86 that are to interact with the cut-outs 80 of the plunger rod $12^{III}$ for creating sound during movement of the plunger rod $12^{III}$. In contrast to the previous embodiment, the plunger rod sleeve 82 is provided with a separate set of arms 88 that are directed in the distal direction and that are flexible in the generally radial direction. The free ends of the arms 88 are provided with inwardly directed ledges 90, which ledges 90 are designed to interact with certain cut-outs $80^I$ in the rows of cut-outs 80 of the plunger rod $12^{III}$. The ledges 90 are arranged to hold the plunger rod $12^{III}$ with a drive spring 36 tensioned as seen in FIG. 10.

The outer ends of the arms 88 are arranged with protrusions 92 that are to interact with an actuator 93 that in the embodiment shown has a tubular body 94 with two distally directed arms 95 slidable inside a housing 96 of a medicament delivery device. When the proximal end of the housing 96 with its extended actuator 93 is pressed against a dose delivery site, the actuator 93 will move in the distal direction and the distal ends of the arms 95 will act on the protrusions 92 and move the arms 88 of the plunger rod sleeve 82 outwardly for releasing the plunger rod $12^{III}$. Moreover, the distal end of the plunger rod $12^{III}$ is provided with a number of outwardly directed guide elements 98, which guide elements 98 are designed to fit into longitudinally extending grooves 99 of the plunger rod sleeve 82 for preventing rotation of the plunger rod $12^{III}$ in relation to the plunger rod sleeve 82.

FIGS. 11-13 show a fourth embodiment of a power pack. In this embodiment a plunger rod sleeve 100 is arranged with two proximally directed arms 102 that are flexible in the generally radial direction. The free ends of the arms 102 are arranged with inwardly directed protrusions 104, FIG. 13, which protrusions 104 fit into recesses 106 of a plunger rod $12^{IV}$ that is slidable inside the plunger rod sleeve 100 for holding the plunger rod $12^{IV}$ in a tensioned state by a drive spring 36. The arms 102 cooperate with an actuator $46^{IV}$ in the same manner as described above.

The plunger rod sleeve 100 is further arranged with signal generating elements in the form of a plurality of proximally directed arms 108 that are flexible in a generally radial direction. The free ends of the arms 108 are arranged with inwardly directed protrusions 110. The plurality of arms 108 is placed in rows after each other in the longitudinal direction of the plunger rod sleeve 100. In the embodiment shown, there are two rows of arms 108 that are placed on opposite sides. The plurality of arms 108 of the signal generating elements is to cooperate with signal initiating elements that are in the form of outwardly directed protrusions 112 on a distal area of the plunger rod $12^{IV}$. The protrusions 112 are placed such that when the plunger rod $12^{IV}$ is released, the protrusions 112 will come in contact with the inwardly directed protrusions 110 of the arms 108 of the signal generating elements, causing an audible feedback that the plunger rod $12^{IV}$ is moving, e.g. during a dose delivery sequence. As with the previous embodiment, if more than one row of arms 108 is used, one row may be placed offset half a step in relation to the other row, creating a higher frequency of the sounds generated.

FIGS. 14-17 show a fifth embodiment of a power pack. As with some of the previous embodiments, a generally tubular plunger rod sleeve 120 is provided with proximally directed arms 122 that are flexible in a generally radial direction. The free ends of the arms 122 are provided with inwardly directed protrusions 124, which protrusions 124 are designed to fit into cut-outs 126 in a generally elongated plunger rod $12^V$, for holding the plunger rod $12^V$ in a tensioned state with a drive spring 36. Also here, an actuator $46^V$ is arranged for interacting with the arms as described above. The proximal end of the plunger rod sleeve 120 is provided with a seat 128 in which a metal clip 130, FIG. 15, can be attached. The metal clip 130 is bent with a certain shape so as to have two arc-shaped sections 132 integrated with inwardly inclined legs 134, which in turn transform into flat sections 136 that attach to the seat. The design provides a flexing action of the arc-shaped sections in a generally longitudinal direction, where the intention is for the arc-shaped sections to be in contact with a distal end of a syringe or the like medicament container for providing a biasing force on the medicament container, thereby minimizing any rattling or movement of the medicament container. In addition, the flat sections 136 are provided with inwardly extending and proximally inclined tongues 138 that constitute signal generating elements.

Further, the plunger rod $12^V$ is arranged with a plurality of circumferentially extending, wedge-shaped, protrusions 140, being sound initiating elements. Thus, when the plunger rod $12^V$ is released and is moved in the proximal direction by a drive spring 36 for performing a dose delivery sequence, the inclined tongues 138 will be in contact with and be tensionally biased by the passing wedge-shaped protrusions 140, hitting subsequent protrusions when leaving previous protrusions, causing tactile and audible information to the user of the ongoing sequence. Since the wedge-shaped protrusions 140 are positioned around the whole circumference of the plunger rod $12^V$, there is no need for guiding elements that orientate the plunger rod $12^V$ in relation to the signal generating element, i.e. the tongues 138.

It is to be understood that the embodiment described above and shown in the drawings is to be regarded only as a non-limiting example of the disclosure and that it may be modified in many ways within the scope of the patent claims.

The invention claimed is:

1. A notification mechanism within a medicament delivery device, where the notification mechanism comprises:
a tubular proximal part having a longitudinal axis and comprising a central opening having an internal surface with an inwardly extending ledge and a longitudinal ledge that projects radially into the central opening; and
a plunger rod positioned within the central opening and comprising a row of signal initiating elements and a groove positioned longitudinally along the plunger rod, wherein the signal initiating elements are arranged one after another in the row longitudinally on the plunger rod, wherein the signal initiating elements are arranged unequally in the row, wherein a recess is aligned with and axially spaced from the row of signal initiating elements to engage with the inwardly extending ledge to releasably hold the plunger rod before activation, and wherein the groove is circumferentially spaced from the signal initiating elements and the recess;
wherein engagement of the longitudinal ledge and the groove rotationally locks the plunger rod with the tubular proximal part to prevent rotation of the plunger rod relative to an outer housing of the medicament delivery device, and
wherein two or more of the signal initiating elements slidably engage with and then disengage from the inwardly extending ledge during relative axial movement between the plunger rod and the tubular proximal part such that a tactile or audible signal notification is provided to a user of the medicament delivery device, where the sequential engagement and disengagement of the inwardly extending ledge with individual ones of the two or more signal initiating elements occurs during delivery of medicament from the medicament delivery device.

2. The notification mechanism of claim 1, wherein the inwardly extending ledge is part of a flexible arm.

3. The notification mechanism of claim 2, wherein the inwardly extending ledge is a protrusion.

4. The notification mechanism of claim 2, wherein the flexible arm is formed from a cut-out in the tubular proximal part.

5. The notification mechanism of claim 3, wherein the flexible arm flexes radially outward away from an outer surface of the tubular proximal part when the protrusion engages with the signal initiating elements.

6. The notification mechanism of claim 1, wherein the inwardly extending ledge and the longitudinal ledge are separated by a radial distance along the internal surface of the central opening.

7. The notification mechanism of claim 1, wherein the row of signal initiating elements comprises a plurality of signal initiating element recesses.

8. The notification mechanism of claim 7, wherein the plurality of signal initiating element recesses are axially spaced wedge-shaped recesses.

9. The notification mechanism of claim 7, wherein the plurality of signal initiating element recesses are formed as cut-outs in an outer surface of the plunger rod.

10. The notification mechanism of claim 1, wherein the signal initiating elements provide a variable notification frequency of the tactile or audible signal notifications.

11. The notification mechanism of claim 10, wherein the variable notification frequency provides notice to the user that a medicament delivery sequence is progressing.

12. The notification mechanism of claim 1, wherein the inwardly extending ledge is a protrusion formed at an end of a flexible arm that is formed from a cut-out in a surface of the tubular proximal part, where the protrusion is shaped to snap into and out of the signal initiating elements during a medicament delivery sequence.

13. The notification mechanism of claim 1, wherein the row of signal initiating elements is positioned at a distal end of the plunger rod such that the user is only notified at an end of a medicament delivery sequence.

14. The notification mechanism of claim 1, wherein the longitudinal ledge is rigidly fixed to the internal surface.

15. The notification mechanism of claim 1, wherein the signal initiating elements and the groove are positioned on an outer surface of the plunger rod such that there is a radial distance between the signal initiating elements and the groove.

16. The notification mechanism of claim 1, wherein the notification mechanism further comprises a spring that causes the relative axial movement between the plunger rod and the tubular proximal part.

17. A medicament delivery device comprising:
an outer housing;
a drive spring within the outer housing having a biased state and a released state; and
a notification mechanism positioned within the outer housing and operatively associated with the drive spring, where the notification mechanism comprises:
 a tubular proximal part having a longitudinal axis and comprising a central opening having an internal surface with an inwardly extending ledge and a longitudinal ledge that project radially into the central opening; and
a plunger rod positioned within the central opening and comprising a row of signal initiating elements and a groove positioned longitudinally along the plunger rod, wherein the signal initiating elements are arranged one after another in the row longitudinally on the plunger rod, and wherein the signal initiating elements are arranged unequally in the row, wherein a recess is aligned with and axially spaced from the row of signal initiating elements to engage with the inwardly extending ledge to releasably hold the plunger rod before activation, wherein the groove is circumferentially spaced from the signal initiating elements and the recess;
wherein engagement of the longitudinal ledge and the groove rotationally locks the plunger rod with the tubular proximal part to prevent rotation of the plunger rod relative to the outer housing of the medicament delivery device, and
wherein when the drive spring transitions from the biased state to the released state two or more of the signal initiating elements slidably engage with and then disengage from the inwardly extending ledge to produce a tactile or audible signal notification to a user of the medicament delivery device, where the sequential engagement and disengagement of the inwardly extending ledge with individual ones of the two or more signal initiating elements occurs during delivery of medicament from the medicament delivery device.

* * * * *